(12) United States Patent
Mahendar et al.

(10) Patent No.: US 9,242,982 B2
(45) Date of Patent: Jan. 26, 2016

(54) PYRIDOPYRIMIDINE BASED DERIVATIVES AS POTENTIAL PHOSPHODIESTERASE 3 (PDE3) INHIBITORS AND A PROCESS FOR THE PREPARATION THEREOF

(71) Applicant: COUNCIL OF SCIENTIFIC & INDUSTRIAL RESEARCH, New Delhi (IN)

(72) Inventors: Budde Mahendar, Hyderabad (IN); Saidulu Mattapally, Hyderabad (IN); Mettu Ravinder, Hyderabad (IN); Sanjay Kumar Banerjee, Hyderabad (IN); Vaidya Jayathirtha Rao, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/168,411

(22) Filed: Jan. 30, 2014

(65) Prior Publication Data

US 2014/0221651 A1    Aug. 7, 2014

(30) Foreign Application Priority Data

Feb. 1, 2013   (IN) ............................ 0288/DEL/2013

(51) Int. Cl.
*C07D 487/04* (2006.01)
*C07D 471/04* (2006.01)
*A61K 31/519* (2006.01)
*A61P 9/06* (2006.01)
*A61P 9/04* (2006.01)

(52) U.S. Cl.
CPC ............ *C07D 471/04* (2013.01); *C07D 487/04* (2013.01)

(58) Field of Classification Search
CPC .................................................... C07D 471/04
See application file for complete search history.

(56) References Cited

PUBLICATIONS

Gowrisankar et al. (Bulletin of the Korean Chemical Society, 2005, 26(2), pp. 319-322).*

* cited by examiner

*Primary Examiner* — Susanna Moore
(74) *Attorney, Agent, or Firm* — Abelman, Frayne & Schwab

(57) ABSTRACT

The present invention provides compounds of formula 1 as potential phosphodiesterase3 (PDE3) inhibitory agents and a process for the preparation thereof. The derivatives of formula 1 can be employed as therapeutics in human and veterinary medicine, where they can be used, for the treatment and prophylaxis of the following diseases: heart failure, dilated cardiomyopathy, platelet inhibitors, cancer and obstructive pulmonary diseases.

Formula 1

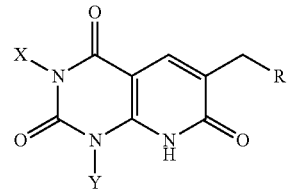

wherein
X=H, alkyl, aryl, or heteroaryl;
Y=H, alkyl, aryl, or heteroaryl;

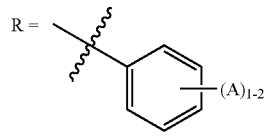

A=alkyl, alkoxy, halo or $CF_3$

3 Claims, 1 Drawing Sheet

Scheme -1

Z = electron withdrawing group
R = H, alkyl, alkoxy, halo, dihalo

Scheme -2

X = H, alkyl, aryl, heteroaryl
Y = H, alkyl, aryl, heteroaryl
Z = electron withdrawing group
R = H, alkyl, alkoxy, halo, dihalo

PYRIDOPYRIMIDINE BASED DERIVATIVES AS POTENTIAL PHOSPHODIESTERASE 3 (PDE3) INHIBITORS AND A PROCESS FOR THE PREPARATION THEREOF

FIELD OF THE INVENTION

The present invention relates to novel pyridopyrimidine based derivatives as potential phosphodiesterase3 (PDE3) inhibitiors and process for the preparation thereof. Particularly, the present invention relates to synthesis of pyridopyrimidine based derivatives of formula 1 and a process for preparing of said compounds.

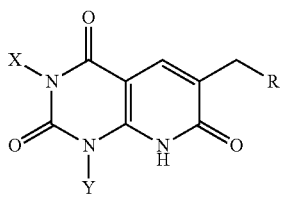

Formula 1

Where in
X=H, alkyl, aryl, heteroaryl
Y=H, alkyl, aryl, heteroaryl
R=substituted phenyl

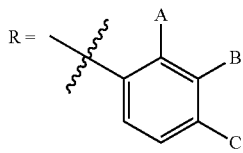

A=H, alkyl, alkoxy, halo, dihalo
B=H, alkyl, alkoxy, halo, dihalo
C=H, alkyl, alkoxy, halo, dihalo More particularly the present invention relates to pyridopyrimidine based derivatives useful as phosphodiesterase3 (PDE3) inhibitory agents. The structural formula of these pyridopyrimidine based derivatives are given below.

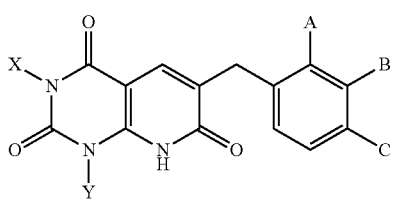

1a-q

BACKGROUND OF THE INVENTION

Congestive heart failure (CHF) is a major cause of death in patients with heart disease. Digitalis glycosides (Drug that is extracted from the leaves of the foxglove plant) have been used for the treatment of CHF for more than 200 years (Gheorghiade, M.; Zarowitz, B. J.; *Am. J. Cardiol.*, 1992, 69, 48G). However, application of these agents are limited because of their narrow therapeutic window and their propensity that cause life-threatening arrhythmias (arrhythmogenic liability). Thus digitalis has been replaced by a new class of cardiotonic agents named as a well known PDE3 inhibitor Amrinonei and Milrinone, a 2-oxopyridine derivative that has been introduced to the clinic for the treatment of CHF in place of digitalis (Kikura, M.; Levy, J. H.; *Int. Anestesiol. Clin.*, 1995, 33, 21). These PDE inhibitors display a greater safety profile and improved efficacy on patient survival.

Phosphodiesterases are a class of intracellular enzymes responsible for the hydrolysis of cyclic adenosine monophosphate (c-AMP) and cyclic guanosine monophosphate (c-GMP) which are involved in the regulation of important cell functions, such as secretion, contraction, metabolism, and growth (Potter, B. V. L.; Transmembrane Signalling Second Messenger Analogues and Inositol Phosphates. In Comprehensive Medical Chemistry; Hansch, C.; Sammes, P. G.; Taylor, J. B., Eds. Pergamon Press: Oxford, 1990; pp 102-128). On the basis of structure, and substrate specificity PDE enzymes can be grouped into eleven different families, PDE1 to PDE11 (Beavo, J. A.; *Physiol. Rev.*, 1995, 75, 725).

Each PDE isozyme has a conserved C-terminal catalytic domain and unique N-terminal regulatory domain. These isozymes are found in different tissues and cells of the humans such as smooth muscle, brain, heart, lung, platelets, lymphocytes etc. and in other species (Bender, A. T.; Beavo, J. A.; *Pharmacol Rev.*, 2006, 58, 488). PDE3 and PDE4 are well established in cardiovascular tissues (Nicholson, C. D.; Challiss, R. A. J.; Shahid, M.; *Trends Phahrmacol Sci.*, 1991, 12, 19). Among all subtypes of PDE, PDE3 is predominantly expressed in heart and platelets. Thus PDE3 play an important role in heart and platelet (Palson, J. B.; Strada, S. J.; *Annu. Rev. Pharmacol. Toxicol.*, 1996, 36, 403).

Inhibition of PDE brings about various physiological reactions, for example inhibition of PDE3 enhances myocardial contraction, produces vasodilatation, and suppresses platelet aggregation (Abadi, A. H.; Ibrahim, T. M.; Abouzid, K. M.; Lehmann, J.; Tinsley, H. N.; Gary, B. D.; Piazza, G. A.; *Bioorg. Med. Chem.* 2009, 17, 5974). These are the reasons why PDE3 inhibitors can be used to treat heart failure.

In addition, the PDE3 isozyme is specific for c-AMP and has no effect on c-GMP and calmodulin. Therefore, inhibition of PDE3 isoenzyme in cardiovascular tissues may lead to high levels of c-AMP and consequent inotropic effect.

Recent studies revealing that PDE3, PDE4, and PDE5 isozymes are over expressed in cancerous cells compared with normal cells. Thus inhibition of PDE3 together with other PDE's may lead to inhibition of tumor cell growth and angiogenesis (Cheng, J. B. and Grande, J. P.; *Exp. Biol. Med.*, 2007, 232, 38).

Recently, PDE3/4 inhibitors have attracted considerable interest as potential therapeutic agents for diseases including chronic obstructive pulmonary disease (COPD). PDE4 or PDE3 inhibitors alone are unable to inhibit spasmogen-induced contraction of human airway, but in combination act synergistically. While PDE3 inhibitor has been shown to inhibit cough, PDE4 inhibitor may be able to stimulate mucociliary clearance. This diverse spectrum of biological effects has thus implicated PDE3/4 inhibitors as potential therapeutic agents for a range of disease indications including COPD. (Banner, K. H.; Press, N.J.; *Br. J. Pharmacol.*, 2009, 157(6): 892-906.)

The present invention describes the synthesis of novel pyridopyrimidine based derivatives as inhibitors of phosphodiesterase3 (PDE3). PDE3 inhibitors are useful for the prevention of heart failure and inhibit platelet aggregation.

The following references are examples for the synthesis and biological evaluation of some of the PDE or PDE3 inhibitors. The prior art contain useful information and discussion on the preparation and properties of PDE inhibitors.

U.S. Pat. No. 5,141,931, reported synthesis of 6-Alkyl-5-(6, or 7-quinolinyl)-3-(substituted)-2(1H)-pyridinones which are useful as cardiotonics. Inhibition of PDE3 was reported to have cardiotonic effect of these compounds.

U.S. Pat. No. 10,151,202, reports novel pyrrolidine compounds that are potent and selective inhibitors of PDE 4, as well as methods development for the synthesis of novel molecules.

Recently our publication reported [Ravinder et al *Bioorg. Med. Chem. Lett.*, (2012)] Synthesis and Evaluation of Novel 2-Pyridone Derivatives as Inhibitors of Phospho-diestarase3 (PDE3): A Target for Heart Failure and Platelet Aggregation.

Ochiai et al., *Bioorg Med. Chem.*, 20(5):1644-1658 (2012) reported synthesis of (−)-6-(7-Methoxy-2-trifluoromethylpyrazolo[1,5-a]pyridin-4-yl)-5-methyl-4,5-dihydro-3-(2H) pyridazinone (KCA-1490), a dual PDE 3/4 inhibitor that exhibits potent combined bronchodilatory and anti-inflammatory activity.

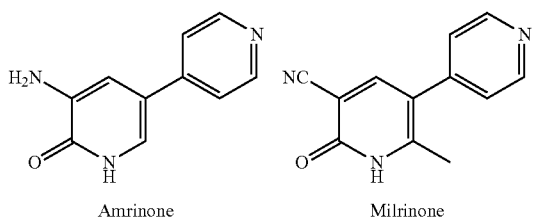

FIG. 1 Phosphorodiesterase3 (PDE$_3$) inhibitors

OBJECTIVES OF THE INVENTION

The main objective of the present invention is to provide novel pyridopyrimidine based analogues useful as potential phosphodiesterase3 (PDE3) inhibitors. Yet another object of this invention is to provide a process for the preparation of novel pyridopyrimidine based derivatives.

SUMMARY OF THE INVENTION

The present invention is directed towards the synthesis of novel pyridopyrimidine based analogues of formula 1 having phosphodiesterase3 (PDE3) inhibition activity.

In an embodiment of the present invention the compound of formula 1, is represented as

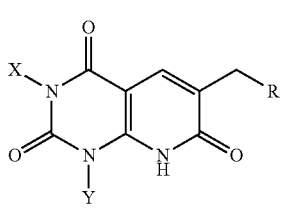

Formula 1

Where in
X=H, alkyl, aryl, heteroaryl
Y=H, alkyl, aryl, heteroaryl
R=substituted phenyl

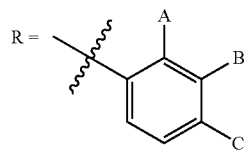

A=H, alkyl, alkoxy, halo, dihalo
B=H, alkyl, alkoxy, halo, dihalo
C=H, alkyl, alkoxy, halo, dihalo In an embodiment of the present invention, the halogen is selected from the group consisting of fluorine, chlorine and bromine.

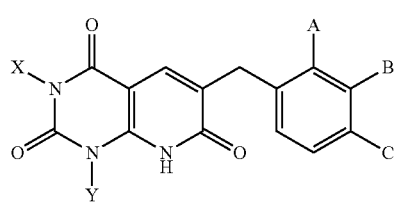

1a-q

In yet another embodiment the compound of formula 1 is one of the following:
6-Benzyl-1,3-dimethylpyrido[2,3-d]pyrimidine-2,4,7(1H, 3H,8H)-trione (1a)
6-(2-Fluorobenzyl)-1,3-dimethylpyrido[2,3-d]pyrimidine-2, 4,7(1H,3H,8H)-trione (1b)
6-(3-Fluorobenzyl)-1,3-dimethylpyrido[2,3-d]pyrimidine-2, 4,7(1H,3H,8H)-trione (1c)
6-(4-Fluorobenzyl)-1,3-dimethylpyrido[2,3-d]pyrimidine-2, 4,7(1H,3H,8H)-trione (1d)
6-(2-Chlorobenzyl)-1,3-dimethylpyrido[2,3-d]pyrimidine-2,4,7(1H,3H,8H)-trione (1e)
6-(3-Chlorobenzyl)-1,3-dimethylpyrido[2,3-d]pyrimidine-2,4,7(1H,3H,8H)-trione (1f)
6-(4-Chlorobenzyl)-1,3-dimethylpyrido[2,3-d]pyrimidine-2,4,7(1H,3H,8H)-trione (1g)
6-(2,4-Dichlorobenzyl)-1,3-dimethylpyrido[2,3-d]pyrimidine-2,4,7(1H,3H,8H)-trione (1h)
6-(2-Bromobenzyl)-1,3-dimethylpyrido[2,3-d]pyrimidine-2,4,7(1H,3H,8H)-trione (1i)
6-(3-Bromobenzyl)-1,3-dimethylpyrido[2,3-d]pyrimidine-2,4,7(1H,3H,8H)-trione (1j)
6-(4-Bromobenzyl)-1,3-dimethylpyrido[2,3-d]pyrimidine-2,4,7(1H,3H,8H)-trione (1k)
1,3-Dimethyl-6-(2-(trifluoromethyl)benzyl)pyrido[2,3-d] pyrimidine-2,4,7(1H,3H,8H)-trione (1l)
1,3-Dimethyl-6-(4-(trifluoromethyl)benzyl)pyrido[2,3-d] pyrimidine-2,4,7(1H,3H,8H)-trione (1m)
1,3-Dimethyl-6-(4-methylbenzyl)pyrido[2,3-d]pyrimidine-2,4,7(1H,3H,8H)-trione (1n)
6-(4-Ethylbenzyl)-1,3-dimethylpyrido[2,3-d]pyrimidine-2, 4,7(1H,3H,8H)-trione (1o)
6-(4-Isopropylbenzyl)-1,3-dimethylpyrido[2,3-d]pyrimidine-2,4,7(1H,3H,8H)-trione (1p)
6-(4-Methoxybenzyl)-1,3-dimethylpyrido[2,3-d]pyrimidine-2,4,7(1H,3H,8H)-trione (1q)

The present invention further provides a process for preparation of compound of formula 1

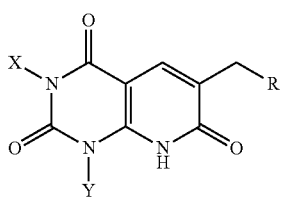

Where in
X=H, alkyl, aryl, heteroaryl
Y=H, alkyl, aryl, heteroaryl
R=substituted phenyl

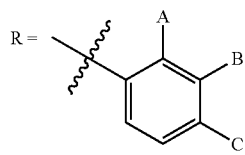

A=H, alkyl, alkoxy, halo, dihalo
B=H, alkyl, alkoxy, halo, dihalo
C=H, alkyl, alkoxy, halo, dihalo, comprising:
a. reacting substituted aromatic aldehyde of formula 2

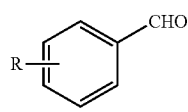

R=H, alkyl, alkoxy, halo, dihalo
with an olefin of formula 3

Z=electron withdrawing group
in presence of a catalyst with stirring and isolating a compound of formula 4;

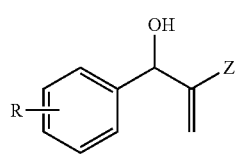

Z=electron withdrawing group
R=H, alkyl, alkoxy, halo, dihalo
b. adding pyridine to the compound of formula 4 of step 1 in presence of an organic solvent under inert atmosphere followed by addition of an acetyl chloride and isolating an acetylated compound of formula 5; and

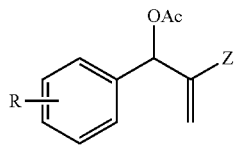

Z=electron withdrawing group
R=H, alkyl, alkoxy, halo, dihalo
c. reacting acetylated compound of formula 5 of step 2 with 2-aminodimethyluracil in an organic solvent and a base and isolating a compound of formula 1.

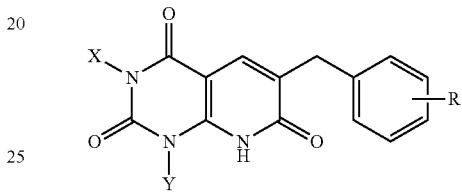

R=H, alkyl, alkoxy, halo, dihalo

The present invention further provides a process for preparation of compound of formula 1a-p, and the said process comprising of following steps 1. reacting an olefin of formula (3a) with a substituted benzaldehydes of formula (2a-q) in presence of a catalyst with stirring and isolating the compound of formula 4a-q.

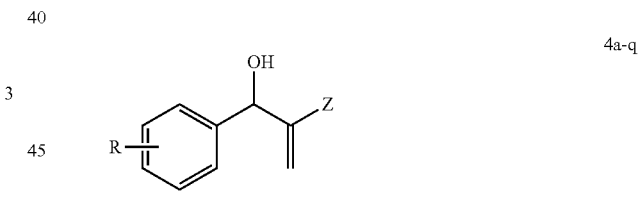

2. adding pyridine to a compound of formula 4 a-q of step 1 in presence of an organic solvent, under inert atmosphere followed by addition of an acetyl chloride and isolating an acetylated compound of formula 5 a-q.

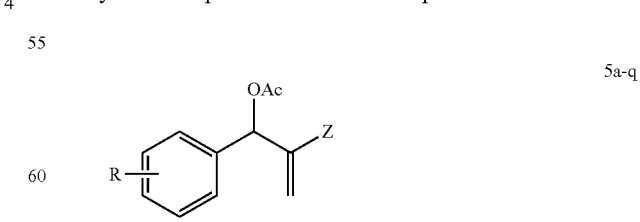

3. reacting an acetylated compounds of formula 5 a-q of step 2 with an 2-aminodimethyluracil of formula 6a in presence of an organic solvent and a base and isolating the compound of formula 1a-q.

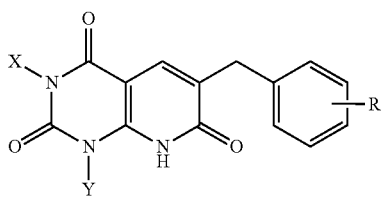

1a-q

In yet another embodiment of the present invention the catalyst is selected from the group consisting of DABCO (1,4-diazabicyclo[2.2.2]octane), quinuclidine 3-HQD (3-hydroxy quinuclidine), 3-quinuclidone, DBU, pyrrocoline, DMAP (dimethylaminopyridine), TMPDA (N,N,N$^1$,N$^1$-tetramethyl-1,3-propanediamine), imidazole, TMG (tetramethyl guanidine), triethyl amine, dimethyl sulfide/TiCl$_4$, TiCl$_4$, trialkylphosphines and RhH(PPh$_3$)$_4$, In yet another embodiment of the present invention the reaction between the substituted aromatic aldehyde of formula 2 and an olefin of formula 3 is carried out at a temperature ranging between 25-35° C.

In another embodiment of the present invention the reaction between the pyridine and a compound of formula 4 in presence of an organic solvent is carried out for a time period ranging between 10-20 min and the reaction between the acetyl chloride with the above said resulting reaction solution is carried out at a temperature ranging between 25-35° C. for a time period ranging between 1-2 hour.

In another embodiment of the present invention, the reaction between the 2-aminodimethyluracil of formula 6 and a compound of formula 5 is carried out for a time period ranging between 7-8 hour.

In another embodiment of the present invention, the base is selected from the group consisting of K$_2$CO$_3$, NaH (100%), NaH (60%), NaOMe, NaOEt and t-BuOK.

In another embodiment of the invention, the organic solvents is selected from the group consisting of ethanol, tetrahydrofuran, acetonitrile and dimethylformamide.

In another embodiment of the invention, the compound of formula 4 is selected from the group consisting of ethyl 2-(hydroxy)(phenyl)methyl)acrylate, ethyl-2-((2-fluorophenyl)(hydroxyl)methyl)acrylate, ethyl-2-((3-fluorophenyl)hydroxyl)methyl)acrylate, ethyl-2-((4fluoropphenyl)hydroxyl)methyl)acrylate, ethyl-2-((2-chlorophenyl)(hydroxyl)methyl)acrylate, ethyl-2((3 cholorophenyl)(hyrdroxy)methyl)acrylate, ethyl-2-((4-chlorophenyl)hydroxyl)methyl)acrylate, ethyl-2-((2,4dicholorophenyl)(hydroxyl)methyl)acrylate, ethyl-2-hydroxy(2-trifluoromethyl)phenyl)methyl)acrylate, ethyl-2(hydroxyl(4(trifluoromethyl)phenyl)methyl)acrylate and ethyl-2(hydroxy)(p-tolyl)methyl)acrylate.

In another embodiment of the invention, the compound of formula 5 is selected from the group consisting of ethyl 2-(acetoxy(phenyl)methyl)acrylate, ethyl 2-(acetoxy(2-fluorophenyl)methyl acrylate, ethyl2-(acetoxy(3-fluorophenyl)methyl)acrylate, ethyl 2-(acetoxy(3-chlorophenyl)methyl) acrylate, ethyl 2-(acetoxy(4-chlorophenyl)methyl)acrylate, ethyl 2-(acetoxy(2,4-dicholrophenyl)methyl)acrylate, ethyl2-(acetoxy(2-bromophenyl)methyl)acrylate, ethyl 2-(acetoxy(3-bromophenyl)methyl)acrylate, ethyl 2-acetoxy (4-bromophenyl)methyl)acrylate, ethyl 2-(acetoxy(2-trifluoromethyl)phenyl)methyl)acrylate, ethyl 2-acetoxy(4-trifluoromethyl)phenyl)methyl)acrylate, ethyl 2-(acetoxy(p-tolyl) methyl)acrylate, ethyl 2-(acetoxy(4-ethylphenyl)methyl) acrylate and ethyl 2-(acetoxy(4-isopropylphenyl)methyl) acrylate.

In another embodiment of the invention, the substituted aromatic aldehyde is selected from the group consisting of alkyl, hydroxyl, halo, dihalo and hydrogen substituted aromatic aldehyde.

In another embodiment of the invention, the compound of formula 1 is used as Phosphodiesterase 3 (PDE3) inhibitory agent.

BRIEF DESCRIPTION OF THE DRAWINGS

The present invention may be more clearly understood by references to the following schemes.

DETAILED DESCRIPTION OF THE INVENTION

Figure 1:
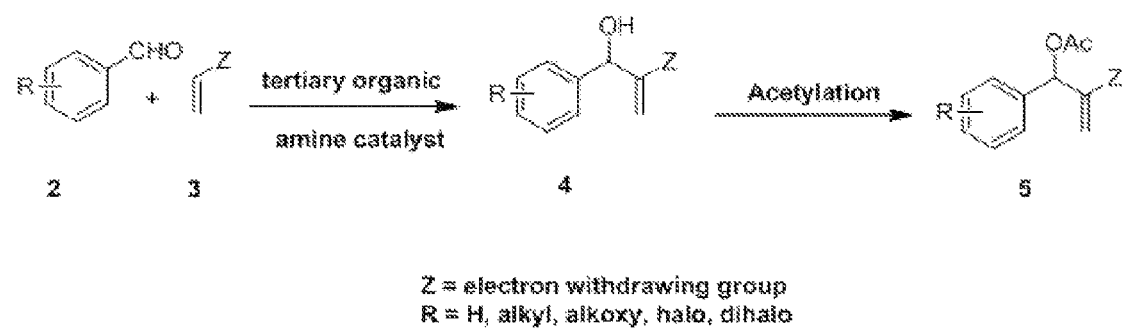
FIG. 1-Scheme 1 illustrates the process for preparation of compound of formula 5.
Figure 2:
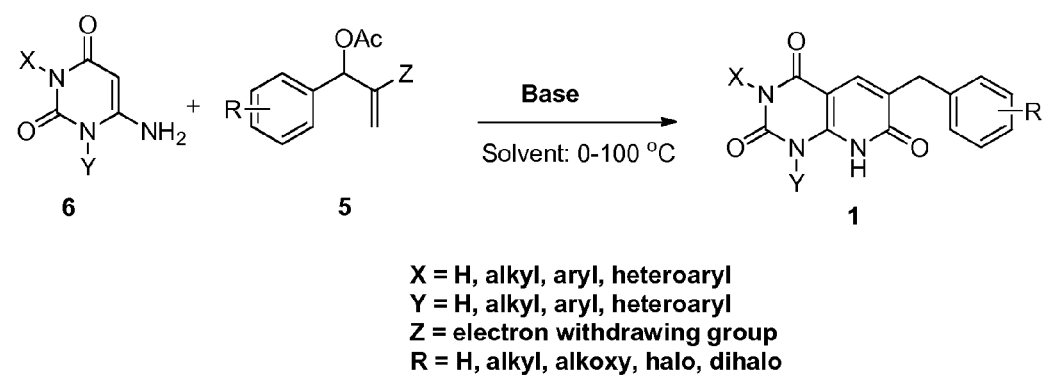
FIG. 2-Scheme 2 illustrates the process for preparation of compound of formula 1.

The precursor substituted aromatic aldehydes (2), activated olefines (3) and 1,4-diazabicyclo[2.2.2]octane (DABCO) are commercially available and the pyridopyrimidines (1), of formula have been prepared as illustrated in the Schemes (1-2).

i. The substituted aromatic aldehydes (2) reacted with the activated olefins (3) using DABCO at room temperature (25-35° C.) for 10-12 h to obtain desired Baylis-Hillman adducts (4).

ii. To a solution of Baylis-Hillman adducts (4) in dichloromethane at 0° C., under argon atmosphere pyridine was added, after 10 min acetyl chloride was added and allow it to stir at room temperature for 2 h to obtain desired acetylated Baylis-Hillman addcuts (5).

All the pyridopyrimidine based derivatives have been synthesized and were purified by column chromatography using solvents like ethyl acetate, hexane, chloroform and methanol.

Procedure of Pyridopyrimidine Formation:

To a solution of 2-aminodimethyluracil (6) in EtOH K$_2$CO$_3$ was added followed by acetylated Baylis-Hillman adducts (5) in EtOH) and allowed to reflux for 8 h. After completion of the reaction, cool it to room temperature, dried over Na$_2$SO$_4$ and diluted with chloroform), filtered the reaction mixture and washed with chloroform. Solvent was removed under reduced pressure and purified by silica gel column chromatography using methanol/chloroform as eluent.

These new analogues of pyridopyrimidine based derivatives were screened for their phosphodiesterase3 inhibitors activity and found as potential phosphodiesterase3 (PDE3) inhibitors. The synthesized molecules presented here are of immense biological significance.

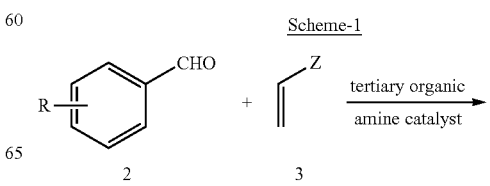

Scheme-1

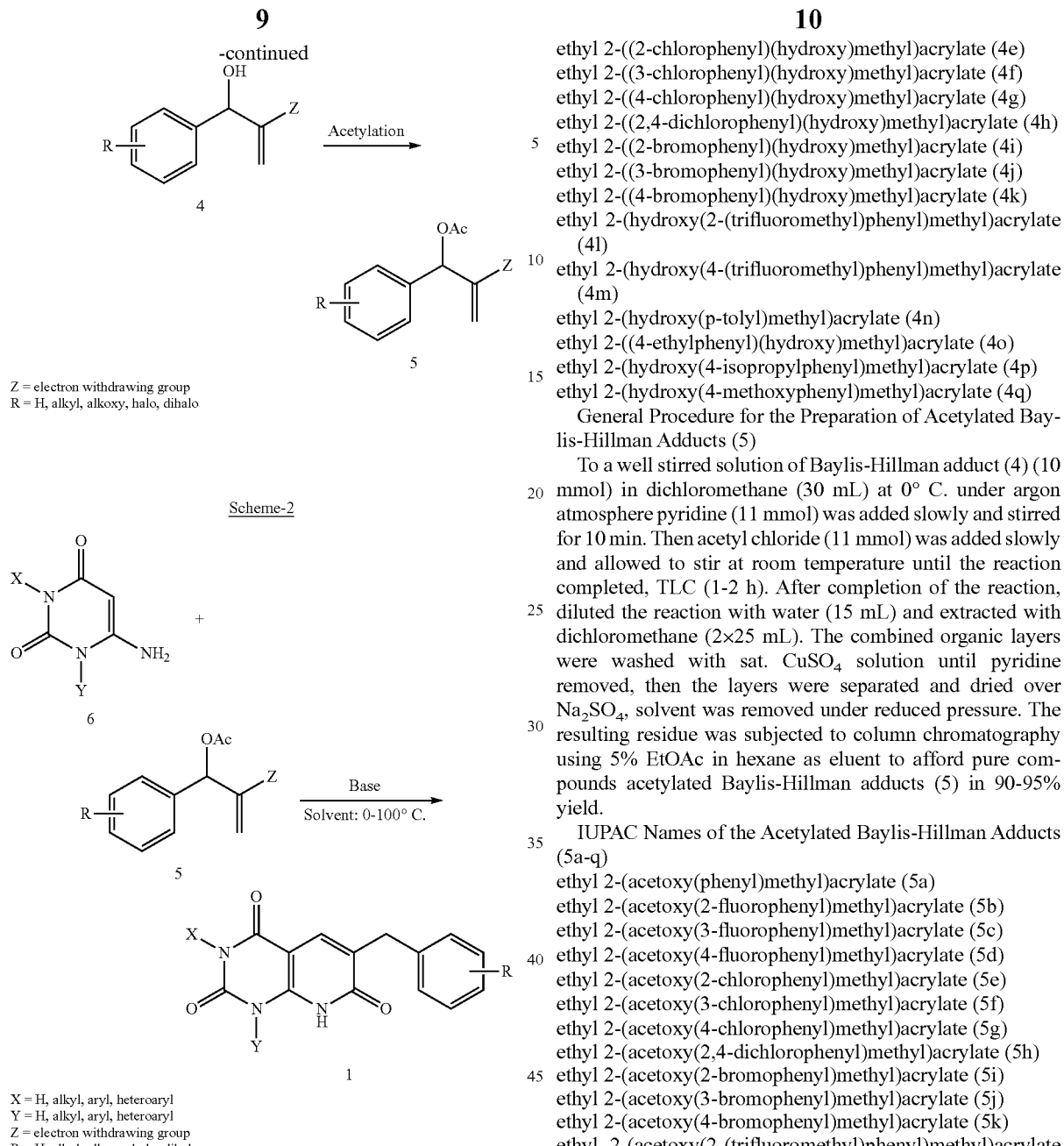

Z = electron withdrawing group
R = H, alkyl, alkoxy, halo, dihalo

Scheme-2

X = H, alkyl, aryl, heteroaryl
Y = H, alkyl, aryl, heteroaryl
Z = electron withdrawing group
R = H, alkyl, alkoxy, halo, dihalo General Procedure for the Preparation Baylis-Hillman Adducts (4)

Substituted aromatic aldehydes (2) (10 mmol), activated olefin (3) (20 mmol) and DABCO (30 mol % with respect to aldehyde) were mixed and allowed to stir at room temperature until completion of the reaction, TLC (10-12 h). After completion, the reaction mixture was diluted with water (15 mL) and extracted with ether (3×25 mL). The combined organic layers were dried over $Na_2SO_4$, solvent was removed under reduced pressure and purified by column chromatography using 10% EtOAc in hexane as eluent to afford pure Baylis-Hillman adducts (4) in 80-90% yield.

IUPAC Names of the Baylis-Hillman Adducts (4a-q)
ethyl 2-(hydroxy(phenyl)methyl)acrylate (4a)
ethyl 2-((2-fluorophenyl)(hydroxy)methyl)acrylate (4b)
ethyl 2-((3-fluorophenyl)(hydroxy)methyl)acrylate (4c)
ethyl 2-((4-fluorophenyl)(hydroxy)methyl)acrylate (4d)
ethyl 2-((2-chlorophenyl)(hydroxy)methyl)acrylate (4e)
ethyl 2-((3-chlorophenyl)(hydroxy)methyl)acrylate (4f)
ethyl 2-((4-chlorophenyl)(hydroxy)methyl)acrylate (4g)
ethyl 2-((2,4-dichlorophenyl)(hydroxy)methyl)acrylate (4h)
ethyl 2-((2-bromophenyl)(hydroxy)methyl)acrylate (4i)
ethyl 2-((3-bromophenyl)(hydroxy)methyl)acrylate (4j)
ethyl 2-((4-bromophenyl)(hydroxy)methyl)acrylate (4k)
ethyl 2-(hydroxy(2-(trifluoromethyl)phenyl)methyl)acrylate (4l)
ethyl 2-(hydroxy(4-(trifluoromethyl)phenyl)methyl)acrylate (4m)
ethyl 2-(hydroxy(p-tolyl)methyl)acrylate (4n)
ethyl 2-((4-ethylphenyl)(hydroxy)methyl)acrylate (4o)
ethyl 2-(hydroxy(4-isopropylphenyl)methyl)acrylate (4p)
ethyl 2-(hydroxy(4-methoxyphenyl)methyl)acrylate (4q)

General Procedure for the Preparation of Acetylated Baylis-Hillman Adducts (5)

To a well stirred solution of Baylis-Hillman adduct (4) (10 mmol) in dichloromethane (30 mL) at 0° C. under argon atmosphere pyridine (11 mmol) was added slowly and stirred for 10 min. Then acetyl chloride (11 mmol) was added slowly and allowed to stir at room temperature until the reaction completed, TLC (1-2 h). After completion of the reaction, diluted the reaction with water (15 mL) and extracted with dichloromethane (2×25 mL). The combined organic layers were washed with sat. $CuSO_4$ solution until pyridine removed, then the layers were separated and dried over $Na_2SO_4$, solvent was removed under reduced pressure. The resulting residue was subjected to column chromatography using 5% EtOAc in hexane as eluent to afford pure compounds acetylated Baylis-Hillman adducts (5) in 90-95% yield.

IUPAC Names of the Acetylated Baylis-Hillman Adducts (5a-q)
ethyl 2-(acetoxy(phenyl)methyl)acrylate (5a)
ethyl 2-(acetoxy(2-fluorophenyl)methyl)acrylate (5b)
ethyl 2-(acetoxy(3-fluorophenyl)methyl)acrylate (5c)
ethyl 2-(acetoxy(4-fluorophenyl)methyl)acrylate (5d)
ethyl 2-(acetoxy(2-chlorophenyl)methyl)acrylate (5e)
ethyl 2-(acetoxy(3-chlorophenyl)methyl)acrylate (5f)
ethyl 2-(acetoxy(4-chlorophenyl)methyl)acrylate (5g)
ethyl 2-(acetoxy(2,4-dichlorophenyl)methyl)acrylate (5h)
ethyl 2-(acetoxy(2-bromophenyl)methyl)acrylate (5i)
ethyl 2-(acetoxy(3-bromophenyl)methyl)acrylate (5j)
ethyl 2-(acetoxy(4-bromophenyl)methyl)acrylate (5k)
ethyl 2-(acetoxy(2-(trifluoromethyl)phenyl)methyl)acrylate (5l)
ethyl 2-(acetoxy(4-(trifluoromethyl)phenyl)methyl)acrylate (5m)
ethyl 2-(acetoxy(p-tolyl)methyl)acrylate (5n)
ethyl 2-(acetoxy(4-ethylphenyl)methyl)acrylate (5o)
ethyl 2-(acetoxy(4-isopropylphenyl)methyl)acrylate (5p)
ethyl 2-(acetoxy(4-methoxyphenyl)methyl)acrylate (5q)

General Procedure for the Preparation of Pyridopyrimidine Derivatives (1)

To a well stirred solution of 2-aminodimethyluracil (6) (1 mmol) in solvent (5 mL) base (415 mg, 3 mmol) was added followed by acetylated Baylis-Hillman adducts (5) (1 mmol) in solvent (5 mL) and allowed to reflux for 7-8 hour and the reaction monitored by TLC. After completion of the reaction cool it to room temperature and diluted with chloroform (10 mL), filter the reaction mixture to remove K2CO3, wash with chloroform (2×5 mL). Solvent was removed under reduced pressure and purified by column chromatography using silica gel with 2% MeOH in $CHCl_3$ as eluent to obtained (1).

The following examples are given by way of illustration

Example 1

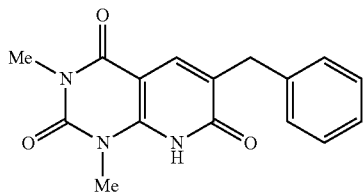

6-Benzyl-1,3-dimethyl-1,2,3,4,7,8-hexahydropyrido[2,3-d]pyrimidine-2,4,7-trione (1a)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(phenyl)methyl)acrylate (5a) (246 mg, 1 mmol) in EtOH (5 mL) and allowed to reflux for 8 h and the reaction monitored by TLC. After completion of the reaction, cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1a as white solid (207 mg, 70% yield).

$^1$H NMR (500 MHz, $CDCl_3$+DMSO-$d_6$): δ 11.95 (br s, 1H), 7.89 (s, 1H), 7.25-7.05 (m, 4H), 3.87 (s, 2H), 3.57 (s, 3H), 3.34 (s, 3H); $^{13}$C NMR (75 MHz, DMSO-$d_6$): δ 164.7, 160.1, 150.8, 139.5, 137.8, 130.1, 128.6, 128.2, 126.0, 118.6, 101.7, 34.2, 29.0, 27.6; MS (ESI): m/z 298 [M+H]$^+$; HRMS (ESI): m/z [M+H]$^+$ calcd for $C_{16}H_{16}N_3O_3$: 298.1191. found: 298.1182.

Example 2

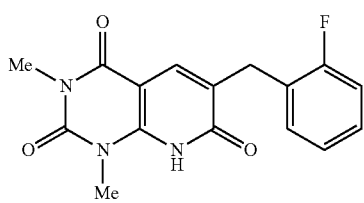

6-(2-Fluorobenzyl)-1,3-dimethyl-1,2,3,4,7,8-hexahydropyrido[2,3-d]pyrimidine-2,4,7-trione (1b)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(2-fluorophenyl)methyl)acrylate (5b) (264 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1b as white solid (238 mg, 76% yield).

$^1$H NMR (500 MHz, $CDCl_3$+DMSO-$d_6$): δ 11.89 (br s, 1H), 7.84 (s, 1H), 7.21-6.99 (m, 4H), 3.88 (s, 2H), 3.55 (s, 3H), 3.32 (s, 3H); $^{13}$C NMR (75 MHz, $CDCl_3$+DMSO-$d_6$): 164.5, 161.9, 160.1, 158.7, 148.3, 137.5, 130.6, 127.6, 123.4, 125.5, 117.5, 114.7, 101.2, 28.8, 27.6, 27.4; MS (ESI): m/z 338 [M+Na]$^+$; HRMS (ESI): m/z [M+Na]$^+$ calcd for $C_{16}H_{14}N_3O_3FNa$: 338.0916. found: 338.0915.

Example 3

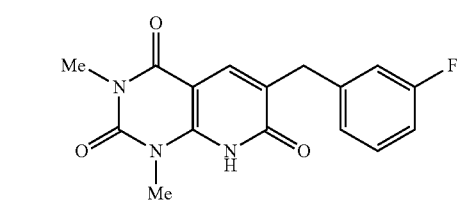

6-(3-Fluorobenzyl)-1,3-dimethyl-1,2,3,4,7,8-hexahydropyrido[2,3-d]pyrimidine-2,4,7-trione (1c)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(3-fluorophenyl)methyl)acrylate (5c) (264 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1c as white solid (226 mg, 72% yield).

$^1$H NMR (400 MHz, $CDCl_3$+DMSO-$d_6$): δ 11.87 (br s, 1H), 7.94 (s, 1H), 7.24-6.84 (m, 4H), 3.88 (s, 2H), 3.56 (s, 3H), 3.40 (s, 3H); $^{13}$C NMR (75 MHz, $CDCl_3$+DMSO-$d_6$): δ 164.6, 163.6, 163.2, 160.1, 150.7, 137.8, 129.4, 124.0, 115.0, 114.8, 112.5, 112.2, 99.6 34.2, 28.8, 27.4; MS (ESI): m/z 338 [M+Na]$^+$; HRMS (ESI): m/z [M+Na]$^+$ calcd for $C_{16}H_{14}N_3O_3FNa$: 338.0878. found: 338.0893.

Example 4

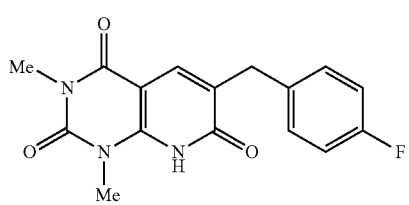

6-(4-Fluorobenzyl)-1,3-dimethyl-1,2,3,4,7,8-hexahydropyrido[2,3-d]pyrimidine-2,4,7-trione (1d)

To a well stirred solution of 2-aminodimethyluracil (6a) (155 mg, x mmol) in EtOH (5 mL) $K_2CO_3$ (415 mg, 3 mmol) was added followed by ethyl 2-(acetoxy(4-fluorophenyl)methyl)acrylate (5d) (264 mg, 1 mmol) in (5 mL) EtOH and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1d as white solid (241 mg, 77% yield).

$^1$H NMR (300 MHz, $CDCl_3$+DMSO-$d_6$): δ 11.78 (br s, 1H), 7.91 (s, 1H), 7.21-6.90 (m, 4H), 3.85 (s, 2H), 3.58 (s, 3H), 3.36 (s, 3H); $^{13}$C NMR (75 MHz, $CDCl_3$+DMSO-$d_6$): δ 163.1, 158.4, 149.2, 136.1, 133.8, 128.5, 128.4, 116.9, 113.2, 112.9, 99.9, 32.0, 27.3, 25.9; MS (ESI): m/z 338 [M+Na]$^+$; HRMS (ESI): m/z [M+Na]$^+$ calculated for $C_{16}H_{14}N_3O_3FNa$: 338.0916. found: 338.0912.

Example 5

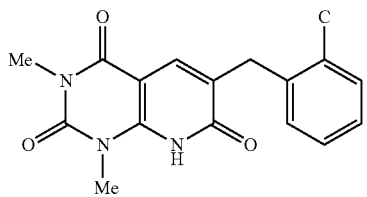

1e 6-(2-Chlorobenzyl)-1,3-dimethyl-1,2,3,4,7,8-hexahydropyrido[2,3-d]pyrimidine-2,4,7-trione (1e)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(2-chlorophenyl)methyl)acrylate (5e) (280 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1e as white solid (244 mg, 74% yield).

$^1$H NMR (300 MHz, $CDCl_3$+DMSO-$d_6$): δ 7.84-7.18 (m, 5H), 3.97 (s, 2H), 3.57 (s, 3H), 3.32 (s, 3H); $^{13}$C NMR (75 MHz, $CDCl_3$+DMSO-$d_6$): δ 164.5, 160.1, 150.7, 148.3, 137.5, 135.9, 133.4, 130.5, 128.8, 127.3, 126.2, 117.3, 101.1, 32.0, 28.8, 27.4; MS (ESI): m/z 332 [M+H]$^+$; HRMS (ESI): m/z [M+H]$^+$ calculated for $C_{18}H_{20}NO_3$: 332.0804. found: 332.0796.

Example 6

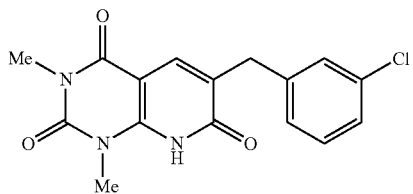

1f 6-(3-Chlorobenzyl)-1,3-dimethyl-1,2,3,4,7,8-hexahydropyrido[2,3-d]pyrimidine-2,4,7-trione (1f)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(3-chlorophenyl)methyl)acrylate (5f) (280 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1f as white solid (237 mg, 72% yield).

$^1$H NMR (300 MHz, DMSO-$d_6$): δ 7.98 (s, 1H), 7.56-7.12 (m, 4H), 3.88 (s, 2H), 3.61 (s, 3H), 3.40 (s, 3H); $^{13}$C NMR (75 MHz, DMSO-$d_6$): δ 164.7, 160.2, 150.9, 142.4, 138.2, 138.1, 132.8, 130.1, 128.3, 127.3, 126.0, 118.0, 103.6, 33.9, 29.1, 27.7; MS (ESI): m/z 332 [M+H]$^+$; HRMS (ESI): m/z [M+Na]$^+$ calculated for $C_{16}H_{14}N_3O_3ClNa$: 354.0621. found: 354.0629.

Example 7

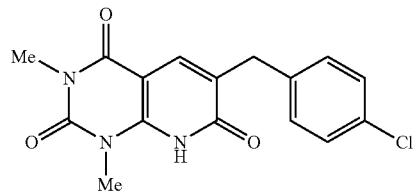

1g 6-(4-Chlorobenzyl)-1,3-dimethyl-1,2,3,4,7,8-hexahydropyrido[2,3-d]pyrimidine-2,4,7-trione (1g)

To a well stirred solution of 2-aminodimethyluracil (6a) (155 mg, 1 mmol) in (5 mL) EtOH $K_2CO_3$ (415 mg, 3 mmol) was added followed by ethyl 2-(acetoxy(4-chlorophenyl)methyl)acrylate (5g) (280 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1g as white solid (257 mg, 78% yield).

$^1$H NMR (300 MHz, $CDCl_3$+DMSO-$d_6$): δ 11.50 (br s, 1H), 7.96 (s, 1H), 7.24-7.16 (m, 4H), 3.86 (s, 2H), 3.61 (s, 3H), 3.41 (s, 3H); $^{13}$C NMR (75 MHz, DMSO-$d_6$): δ 164.8, 160.1, 150.8, 148.9, 138.2, 137.9, 130.9, 130.1, 128.0, 118.2, 102.1, 33.8, 29.0, 27.6; MS (ESI): m/z 332 [M+H]$^+$; HRMS (ESI): m/z [M+Na]$^+$ calculated for $C_{16}H_{14}N_3O_3ClNa$: 354.0621. found: 354.0606.

Example 8

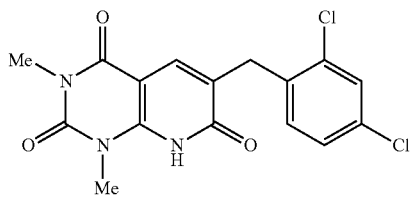

6-(2,4-Dichlorobenzyl)-1,3-dimethyl-1,2,3,4,7,8-hexahydropyrido[2,3-d]pyrimidine-2,4,7-trione (1h)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(2,4-dichlorophenyl)methyl) acrylate (5h) (315 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1h as white solid (291 mg, 80% yield).

$^1$H NMR (300 MHz, $CDCl_3$+DMSO-$d_6$): δ 11.9 (br s, 1H), 7.8 (s, 1H), 7.38-7.18 (s, 1H), 7.18 (s, 2H), 3.49 (s, 2H), 3.58 (s, 3H), 3.51 (s, 3H). $^{13}$C NMR (300 MHz, $CDCl_3$+DMSO-$d_6$): δ 164.0, 159.6, 150.2, 148.0, 137.1, 134.4, 133.7, 131.5, 131.0, 128.0, 126.0, 116.0, 100.7, 31.1, 28.3, 26.9. MS (ESI): m/z 388 [M+Na]$^+$. HRMS (ESI): m/z [M+Na]$^+$ calcd for $C_{16}H_{13}N_3O_3Cl_2Na$: 388.0231. found: 388.0235.

Example 9

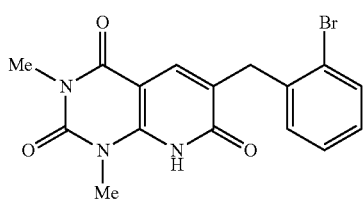

6-(2-Bromobenzyl)-1,3-dimethyl-1,2,3,4,7,8-hexahydropyrido[2,3-d]pyrimidine-2,4,7-trione (1i)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(2-bromophenyl)methyl)acrylate (5i) (324 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1i as white solid (288 mg, 77% yield).

$^1$H NMR (500 MHz, $CDCl_3$+DMSO-$d_6$): δ 11.94 (br s, 1H), 7.70 (s, 1H), 7.56-7.11 (m, 4H), 3.94 (s, 2H), 3.54 (s, 3H), 3.28 (s, 3H). $^{13}$C NMR (75 MHz, $CDCl_3$+DMSO-$d_6$): δ 163.4, 158.7, 149.4, 147.4, 136.6, 136.2, 131.0, 129.5, 126.7, 126.0, 122.8, 115.5, 100.1, 33.3, 27.6, 26.2. MS (ESI): m/z 376 [M+H]$^+$. HRMS (ESI): m/z [M+Na]$^+$ calculated for $C_{16}H_{14}N_3O_3BrNa$: 398.0116. found: 398.0115.

Example 10

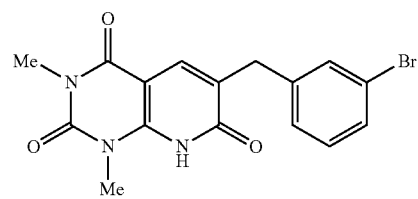

6-(3-Bromobenzyl)-1,3-dimethyl-1,2,3,4,7,8-hexahydropyrido[2,3-d]pyrimidine-2,4,7-trione (1j)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(3-bromophenyl)methyl)acrylate (5j) (324 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1j as white solid (273 mg, 73% yield).

$^1$H NMR (500 MHz, $CDCl_3$+DMSO-$d_6$): δ 7.97 (s, 1H), 7.37-7.15 (m, 3H), 3.87 (s, 2H), 3.57 (s, 3H), 3.55 (s, 3H); $^{13}$C NMR (75 MHz, $CDCl_3$+DMSO-$d_6$): δ 164.6, 160.1, 150.7, 148.7, 141.7, 137.9, 130.9, 129.6, 128.6, 127.1, 121.5, 117.9, 101.3, 34.1, 28.8, 27.4; MS (ESI): m/z 376 [M+H]$^+$. HRMS (ESI): m/z [M+Na]$^+$ calculated for $C_{16}H_{14}N_3O_3BrNa$: 398.0116. found: 398.0110.

Example 11

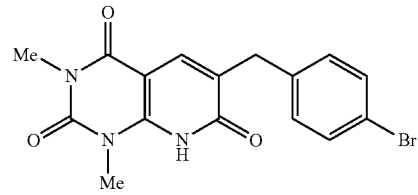

6-(4-Bromobenzyl)-1,3-dimethyl-1,2,3,4,7,8-hexahydropyrido[2,3-d]pyrimidine-2,4,7-trione (1k)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(4-bromophenyl)methyl)acrylate (5k) (324 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in CHCl$_3$ as eluent to obtained 1k as white solid (302 mg, 81% yield).

$^1$H NMR (300 MHz, CDCl$_3$+DMSO-d$_6$): δ 11.91 (br s, 1H), 7.91 (s, 1H), 7.38-712 (d, 2H), 7.12 (d, 2H), 3.38 (s, 2H), 3.55 (s, 3H), 3.33 (s, 3H). $^{13}$C NMR (75 MHz, CDCl$_3$+DMSO-d$_6$): δ 164.5, 160.1, 150.7, 148.5, 138.0, 137.7, 130.7, 130.1, 119.2, 118.3, 101.2, 33.9, 28.8, 27.4; MS (ESI): m/z 376 [M+H]$^+$. HRMS (ESI): m/z [M+Na]$^+$ calcd for C$_{16}$H$_{14}$N$_3$O$_3$BrNa: 397.9990. found: 397.9994.

Example 12

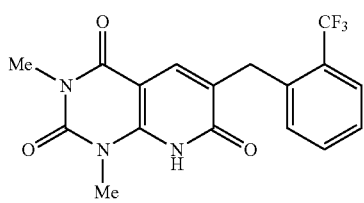

1l 1,3-Dimethyl-[2-(trifluoromethyl)benzyl]-1,2,3,4,7,8-hexahydropyrido[2,3-d]pyrimidine-2,4,7-trione (1l)

To a well stirred solution of 2-aminodimethyluracil (6a) (155 mg, 1 mmol) in EtOH (5 mL) K$_2$CO$_3$ (415 mg, 3 mmol) was added followed by ethyl 2-(acetoxy(2-(trifluoromethyl)phenyl)methyl)acrylate (5l) (314 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove K$_2$CO$_3$, wash with chloroform (2×5 mL). Solvent was removed under reduced pressure and purified by column chromatography using silica gel with 2% MeOH in CHCl$_3$ as eluent to obtained 1l as white solid (273 mg, 75% yield).

$^1$H NMR (300 MHz, CDCl$_3$+DMSO-d$_6$): δ 7.81 (s, 1H), 7.69-7.20 (m, 3H), 4.07 (s, 2H), 3.59 (s, 3H), 3.32 (s, 3H); $^{13}$C NMR (75 MHz, CDCl$_3$+DMSO-d$_6$): δ 163.2, 158.7, 149.4, 147.5, 136.4, 135.8, 130.6, 129.7, 126.6, 126.3, 125.1, 124.3, 120.9, 116.1, 29.5, 27.6, 26.2. MS (ESI): m/z 366 [M+H]$^+$. HRMS (ESI): m/z calcd for C$_{18}$H$_{20}$NO$_3$ [M+H]$^+$: 366.1065. found: 366.1060.

Example 13

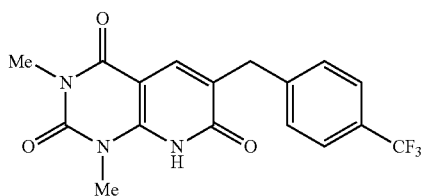

1m 1,3-Dimethyl-[4-(trifluoromethyl)benzyl]-1,2,3,4,7,8-hexahydropyrido[2,3-d]pyrimidine-2,4,7-trione (1m)

To a well stirred solution of 2-aminodimethyluracil (6a) (155 mg, 1 mmol) in EtOH (5 mL) K$_2$CO$_3$ (415 mg, 3 mmol) was added followed by ethyl 2-(acetoxy(4-(trifluoromethyl)phenyl)methyl)acrylate (5m) (314 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove K$_2$CO$_3$, wash with chloroform (2×5 mL). Solvent was removed under reduced pressure and purified by 1 column chromatography using silica gel with 2% MeOH in CHCl$_3$ as eluent to obtained 1m as white solid (280 mg, 77% yield).

$^1$H NMR (300 MHz, CDCl$_3$+DMSO-d$_6$): δ 11.85 (br s, 1H), 7.97 (s, 1H), 7.50 (s, 2H), 7.39 (s, 2H), 3.95 (s, 2H), 3.57 (s, 3H), 3.35 (s, 3H). $^{13}$C NMR (75 MHz, CDCl$_3$+DMSO-d$_6$): δ 164.1, 159.6, 150.2, 148.1, 142.9, 137.4, 128.2, 124.1, 124.1, 121.4, 117.4, 100.8, 33.9, 28.8, 26.9; MS (ESI): m/z 366 [M+H]$^+$. HRMS (ESI): m/z [M+H]$^+$ calculated for C$_{17}$H$_{15}$N$_3$O$_3$F$_3$: 366.1065. found: 366.1047.

Example 14

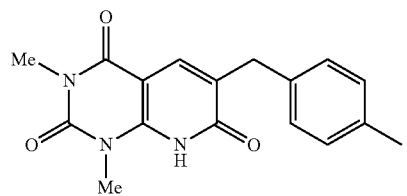

1n 1,3-Dimethyl-6-(4-methylbenzyl)-1,2,3,4,7,8-hexahydropyrido[2,3-d]pyrimidine-2,4,7-trione (1n)

To a well stirred solution of 2-aminodimethyluracil (6a) (155 mg, 1 mmol) in EtOH (5 mL) K$_2$CO$_3$ (415 mg, 3 mmol) was added followed by ethyl 2-(acetoxy(p-tolyl)methyl)acrylate (5n) (260 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove K$_2$CO$_3$, wash with chloroform (2×5 mL). Solvent was removed under reduced pressure and purified by column chromatography using silica gel with 2% MeOH in CHCl$_3$ as eluent to obtained in as white solid (235 mg, 76% yield).

$^1$H NMR (300 MHz, CDCl$_3$+DMSO-d$_6$): δ 11.9 (br s, 1H), 8.01 (s, 1H), 7.52-7.37 (m, 4H), 3.81 (s, 2H), 3.55 (s, 3H), 3.40 (s, 3H). $^{13}$C NMR (75 MHz, CDCl$_3$+DMSO-d$_6$): δ 164.9, 160.0, 150.6, 148.1, 136.9, 135.5, 134.5, 128.1, 127.9, 119.3, 100.5, 33.8, 28.4, 27.1, 20.0. MS (ESI): m/z 334 [M+Na]$^+$. HRMS (ESI): m/z [M+Na]$^+$ calculated for C$_{17}$H$_{17}$N$_3$O$_3$Na: 334.1167. found: 334.1151.

Example 15

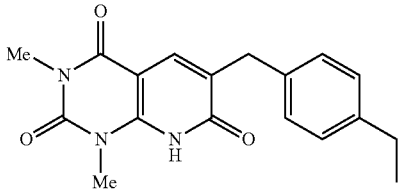

6-(4-Ethylbenzyl)-1,3-dimethyl-1,2,3,4,7,8-hexahydropyrido[2,3-d]pyrimidine-2,4,7-trione (1o)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(4-ethylphenyl)methyl)acrylate (5o) (274 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1o as white solid (240 mg, 74% yield).

$^1$H NMR (300 MHz, $CDCl_3$+DMSO-$d_6$): δ 11.64 (br s, 1H), 7.87 (s, 1H), 7.11-7.04 (m, 4H), 3.82 (s, 2H), 3.56 (s, 3H), 3.33 (s, 3H), 2.60 (q, 2H), 1.23 (t, 3H). $^{13}$C NMR (75 MHz, DMSO-$d_6$): δ 164.4, 160.0, 150.6, 148.1, 141.2, 137.5, 135.8, 128.1, 127.2, 119.3, 95.4, 34.0, 28.7, 27.7, 27.3, 15.0. MS (ESI): m/z 348 [M+Na]$^+$. HRMS (ESI): m/z [M+Na]$^+$ calculated for $C_{18}H_{19}N_3O_3Na$: 348.1324. found: 348.1310.

Example 16

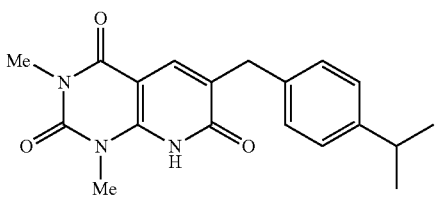

6-(4-Isopropylbenzyl)-1,3-dimethyl-1,2,3,4,7,8-hexahydropyrido[2,3-c]pyrimidine-2,4,7-trione (1p)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(4-isopropylphenyl)methyl)acrylate (5p) (288 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1p as white solid (236 mg, 70% yield).

$^1$H NMR (300 MHz, $CDCl_3$+DMSO-$d_6$): δ 10.40 (br s, 1H), 7.74-7.29 (m, 5H), 3.74 (s, 2H), 3.48 (s, 3H), 3.27 (s, 3H). $^{13}$C NMR (75 MHz, DMSO-$d_6$): δ 165.0, 160.5, 151.2, 149.1, 146.3, 138.0, 137.1, 128.8, 126.4, 119.2, 101.9, 34.1, 33.2, 29.3, 28.0, 24.1. MS (ESI): m/z 362 [M+Na]$^+$. HRMS (ESI): m/z [M+Na]$^+$ calculated for $C_{19}H_{21}N_3O_3Na$: 362.1480. found: 362.1467.

Example 17

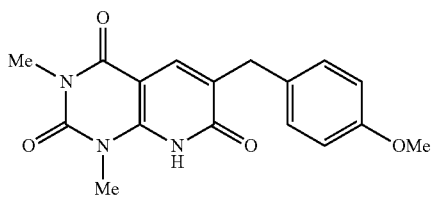

6-(4-Methoxybenzyl)-1,3-dimethyl-1,2,3,4,7,8-hexahydropyrido[2,3-d]pyrimidine-2,4,7-trione (1q)

To a well stirred solution of 2-aminodimethyluracil (6a) (155 mg, 1 mmol) in EtOH (5 mL) $K_2CO_3$ (415 mg, 3 mmol) was added followed by ethyl 2-(acetoxy(4-methoxyphenyl)methyl)acrylate (5q) (276 mg, 1 mmol) in EtOH (5 mL) and allowed to reflux for 8 h and the reaction monitored by TLC. After completion of the reaction cool it to room temperature and diluted with chloroform (10 mL), filter the reaction mixture to remove $K_2CO_3$, wash with chloroform (2×5 mL). Solvent was removed under reduced pressure and purified by column chromatography using silica gel with 2% MeOH in $CHCl_3$ as eluent to obtained 1q as white solid (225 mg, 69% yield).

$^1$H NMR (300 MHz, DMSO-$d_6$): δ 10.35 (br s, 1H), 7.77 (s, 1H), 7.51-6.99 (m, 5H), 3.85 (s, 3H), 3.07 (s, 2H), 3.47 (s, 3H), 3.26 (s, 3H); $^{13}$C NMR (75 MHz, DMSO-$d_6$): δ 165.0, 163.5, 160.5, 157.8, 151.2, 132.5, 131.5, 129.9, 114.4, 113.9, 101.9, 55.1, 33.6, 29.3, 28.0; MS (ESI): m/z 328 [M+H]$^+$; HRMS (ESI): m/z [M+H]$^+$ calculated for $C_{17}H_{18}N_3O_4$: 328.1297. found: 328.1308.

Pharmacology

Milrinone, a known PDE3 inhibitor, drug has been used as standard for comparison with the inhibitory activity of synthesized new analogues 1a-q. Milrinone is a nonsympathomimetic and nonglycosidic drug that increases myocardial contraction. It increases myocardial cyclic adenosine monophosphate (c-AMP) concentration by selective inhibition of cardiac phosphodiesterase3 (PDE3) enzymes and increases intracellular calcium level, thereby increasing myocardial contractility (Weishaar R E, Quade M M, Schenden J A, Evans D B.

Relationship between inhibition of cardiac muscle phosphodiesterase, changes in cyclic nucleotide levels, and contractile response for Cl-914 and other novel cardiotonics. (J Cyclic Nucleotide Protein Phosphor Res 1985; 10:551-64). All PDE3 inhibitors has beneficial effects on the acute treatment of congestive heart failure (Bairn D S, McDowell A V, Chemiles J, et al. Evaluation of a new bipyridine inotropic agent-milrinone-in patients with severe congestive heart failure. N Engl J Med 1983; 309:748-56) and offers an important therapeutic option for left ventricular failure in patients undergoing cardiac surgery because of its unique inodilator effects. PDE3 enzymes are present not only in cardiac muscle but it also present in platelets. In platelets, c-AMP generated from adenosine triphosphate by adenyl cyclase serves as an intracellular second messenger to inhibit the platelet activation at numerous steps (Campbell F W, Addonizo V P Jr. Platelet function alterations during cardiac surgery. In: Ellison N, Jobes D R, ed. Effective hemostasis in cardiac surgery. Philadelphia: WB Saunders, 1988: 93-5). Since abnormal bleeding after cardiopulmonary bypass (CPB) is most often due to an acute acquired defect in platelets (Harker L. Bleeding after cardiopulmonary bypass. N Engl J Med 1986; 314: 1446-8), preservation of platelet function is critical to maintaining normal hemostasis in patients undergoing cardiac surgery.

The commercially utility of the compounds according to the invention have valuable pharmacological properties. As selective inhibitors of type 3 of cyclic nucleotide phosphodiesterase3 (PDE3), they are suitable for heart failure therapy as well as anti-thrombotic (platelet aggregation-inhibiting) therapy.

Biological Investigations

PDE3 inhibition assay was performed a BIOMOL GREEN™ Quantizyme Assay System (catalogue No. BML-AK800-0001). The Platelets isolated from human blood were used as a source of PDE3 enzyme. 10 mL blood collected in a vacutainer tube (containing $K_3$ EDTA) and centrifuged at 190×g for 15 min at room temperature. Top layer (platelet rich plasma) collected, centrifuged at 2500 g for 5 min at 22° C. (Room temp.) The pellet was washed with 2 ml of 50 mM tris buffer (pH-7.4) containing 1 mM $MgCl_2$ and centrifuged at 2500 g for 5 min. Then 200 μl of assay buffer (from PDE kit, Enzo Life Sciences) was added to the pellet and sonicated at 30 s per ml. Pellet was freeze thawed for three times (−80° C.) in order to rupture the platelet membrane and release the PDE enzyme. Then the cell homogenate was centrifuged at 2500 rpm for 5 min. Supernatant was collected and used as source for PDE3 enzyme. In 96 well plate (Prod. No. BML-KI101), we added supernatant having PDE3 enzyme, PDE3 assay buffer, cAMP substrate, 5' nucleotidase and test or standard compound and incubated for 1 hour at 37° C. The reaction was arrested by the addition 100 μl BIOMOL GREEN reagent incubated in room temp for 20 min. The green color developed was measured at 620 nm.

Methodology

The in vitro Phosphodiestarase (PDE3) inhibitory activity of compounds 1a-q, were measured using a BIOMOL GREEN™ Quantizyme Assay System (catalogue No. BML-AK800-0001). The basic principle for this assay is the cleavage of c-AMP or c-GMP into their respective nucleotide by a cyclic nucleotide phosphodiesterase. The nucleotide (AMP or GMP) released is further cleaved into the nucleoside and phosphate by the enzyme 5'-nucleotidase. The extent of phosphate released is directly proportional to the PDE activity. In this screening method, the released phosphate by the enzymatic cleavage is quantified using BIOMOL GREEN reagent in a modified malachite green assay. The resulting green colour with λmax at 620 nm is directly proportional to the released phosphate and then PDE activity. All the compounds tested in the desired concentrations did not show any significant absorbance at 620 nm under control conditions. Milrinone, a known PDE3 inhibitor drug has been used as a standard compound for comparison with the inhibitory activity of newly synthesized analogues. The concentration with 50% PDE3 activity ($IC_{50}$) of all tested compounds was calculated from dose response curves. $IC_{50}$ values of all compounds are summarized in Table 1.

TABLE 1

PDE3 inhibitory activity ($IC_{50}$) of Pyridopyrimidine derivatives.

| S. No | Compound Name | $IC_{50}$(PDE3) |
|---|---|---|
| 1 | Milrinone | 3300 nM |
| 2 | 1a | 11800 nM |
| 3 | 1b | 48.80 nM |
| 4 | 1c | 32.30 nM |
| 5 | 1g | 12.50 nM |
| 6 | 1i | 6.600 nM |
| 7 | 1k | 4.800 nM |

Significance of the Work Carried Out

The novel pyridopyrimidine based analogues have been synthesized, exhibited potent phosphodiesterase3 (PDE3) inbition activity.

Advantages of the Invention

1. The present invention provides the synthesis of new pyridopyrimidine analogues useful as phosphodiesterase3 inhibitory agents.
2. The present invention provides a process for the preparation of novel pyridopyrimidine derivatives.
3. It is an another advantage that Baylis-Hillman adducts used as synthons for the synthesis of targeted compounds.
4. It is an another advantage that the synthesized compounds are heterocyclic compound are heterocyclic derivatives.
5. It is an another advantage that the compounds are useful as cardiotonics.
6. It is an another advantage that bases utilised for the synthons are simple and base are commercially available.
7. It is an advantage that the method used for the synthesis of compounds is novel.

We claim:

1. A compound having formula 1

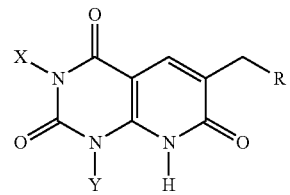

formula 1 wherein
X=H, alkyl, aryl, or heteroaryl;
Y=H, alkyl, aryl, or heteroaryl; and

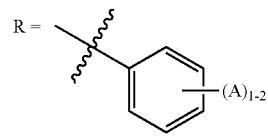

wherein
A=alkyl, alkoxy, halo, or $CF_3$.

2. The compound as claimed in claim 1, wherein the halogen is selected from the group consisting of fluorine, chlorine and bromine.

3. The compound as claimed in claim 1, which is selected from the group consisting of:

6-(2-Fluorobenzyl)-1,3-dimethylpyrido[2,3-d]pyrimidine-2,4,7(1H,3H,8H)-trione, (1b)
6-(3-Fluorobenzyl)-1,3-dimethylpyrido[2,3-d]pyrimidine-2,4,7(1H,3H,8H)-trione, (1c)
6-(4-Fluorobenzyl)-1,3-dimethylpyrido[2,3-d]pyrimidine-2,4,7(1H,3H,8H)-trione, (1d)
6-(2-Clorobenzyl)-1,3-dimethylpyrido[2,3-d]pyrimidine-2,4,7(1H,3H,8H)-trione, (1e)
6-(3-Chlorobenzyl)-1,3-dimethylpyrido[2,3-d]pyrimidine-2,4,7(1H,3 H,8H)-trione, (1f)
6-(4-Chlorobenzyl)-1,3-dimethylpyrido[2,3-d]pyrimidine-2,4,7(1H,3 H,8H)-trione, (1g)
6-(2,4-Chlorobenzyl-1,3-dimethylpyrido[2,3-d]pyrimidine-2,4,7(1H,3H,8H)-trione, (1h)
6-(2-Bromobenzyl)-1,3-dimethylpyrido[2,3-d]pyrimidine-2,4,7(1H,3H,8H)-trione, (1i)
6-(3-Bromobenzyl)-1,3-dimethylpyrido[2,3-d]pyrimidine-2,4,7(1H,3H,8H)-trione, (1j)
6-(4-Bromobenzyl)-1,3-dimethylpyrido[2,3-d]pyrimidine-2,4,7(1H,3H,8H)-trione, (1k)
1,3-Dimethyl-6-(2-(trifluromethyl)benzyl)pyrido[2,3-d]pyrimidine-2,4,7(1H,3,H,3H)-trione, (1l)
1,3-Dimethyl-6-(4-(trifluoromethyl)benzyl)pyrido[2,3-d]pyrimidine-2,4,7(1H,3H,8H)-trione, (1m),
1,3Dimethyl-6-(4-methylbenzyl)-pyrido[2,3-d]pyrimidine-2,4,7(1H,3H,8H)-trione (1n),
6-(4-Ethylbenzyl)-1,3-dimethylpyrido[2,3-d]pyrimidine-2,4,7(1H,3H,8H)-trione (1o),
6-(4-Isopropylbenzyl)-1,3-dimethylpyrido[2,3-d]pyrimidine-2,4,7(1H,3H,8H)-trione (1p), and
6-(4-Methoxybenzyl)-1,3-dimethylpyrido[2,3-d]pyrimidine-2,4,7(1H,3H,8H)-trione (1q).

\* \* \* \* \*